United States Patent [19]
Maracas et al.

[11] Patent Number: 6,048,692
[45] Date of Patent: *Apr. 11, 2000

[54] SENSORS FOR ELECTRICALLY SENSING BINDING EVENTS FOR SUPPORTED MOLECULAR RECEPTORS

[75] Inventors: George N. Maracas, Phoenix; Travis Johnson, Chandler, both of Ariz.

[73] Assignee: Motorola, Inc., Schaumburg, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/946,620

[22] Filed: Oct. 7, 1997

[51] Int. Cl.[7] .................................................. C12Q 1/68

[52] U.S. Cl. .............................. 435/6; 435/91.2; 536/21.3

[58] Field of Search ....................... 435/6, 91.2; 536/21.3

[56] References Cited

U.S. PATENT DOCUMENTS

| | | | |
|---|---|---|---|
| 5,436,170 | 7/1995 | Cornell et al. | 436/527 |
| 5,527,703 | 6/1996 | Cully et al. | 435/252.3 |
| 5,653,939 | 8/1997 | Hollis et al. | 422/50 |

*Primary Examiner*—Scott W. Houtteman
*Attorney, Agent, or Firm*—James E. Gauger

[57] ABSTRACT

A first sensor (18) for electrically sensing a molecular binding event includes a receptor-supporting element (20) into which a reagent is diffusable, at least one molecular receptor (22) supported by the receptor-supporting element (20), and a first electrode (24) embedded in the receptor-supporting element (20). A second sensor for electrically sensing a molecular binding event includes a receptor-supporting element (130), at least one molecular receptor (132) supported by the receptor-supporting element (130), an electrode (134) coupled to the receptor-supporting element (130), and a porous electrode (136) coupled to the receptor-supporting element (130).

24 Claims, 4 Drawing Sheets

SENSORS FOR ELECTRICALLY SENSING BINDING EVENTS FOR SUPPORTED MOLECULAR RECEPTORS

TECHNICAL FIELD

The present invention relates to sensors for electrically sensing binding events with supported molecular receptors.

BACKGROUND OF THE INVENTION

U.S. Pat. No. 5,552,270 to Khrapko et al. describes a device for sequencing DNA by hybridization. The device comprises an oligonucleotide array rigidly bound to a solid substrate. The oligonucleotide array consists of a multiplicity of gel portions separated from one another. Each gel portion contains one oligonucleotide of desired length.

Test DNA fragments are labeled with either a radioactive marker or a fluorescent marker. A solution including a buffer and the labeled test DNA fragments is applied to the device. The solution fully covers the gel portions containing immobilized oligonucleotides. The labeled test DNA fragments hybridize with one or more of the oligonucleotides. After performing a washing step, hybridization events are detected by detecting the radioactive marker or the fluorescent marked. A sequence associated with the test DNA fragments is reconstructed by analyzing detection data.

It is desirable to detect the hybridization events without requiring that the test DNA fragments be labeled with radioactive markers or fluorescent markers.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Figure 1:
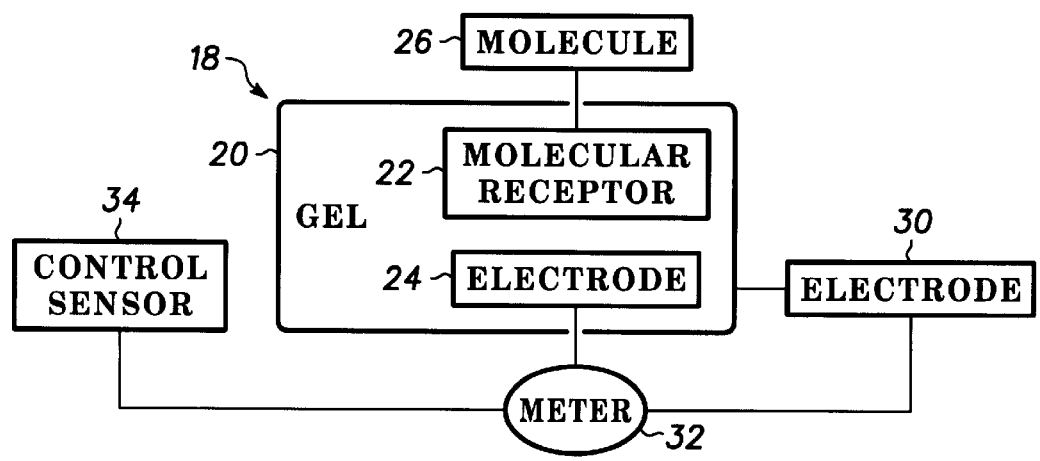
FIG. 1 is a block diagram of a sensor in accordance with the present invention.

FIG. 1 is a block diagram of a sensor 18 in accordance with the present invention; The sensor 18 comprises a gel 20 which supports at least one molecular receptor 22. Preferably, the gel 20 supporting the at least one molecular receptor 22 is formed in accordance with U.S. Pat. No. 5,552,270 to Khrapko et al. which is hereby incorporated by reference into the present application.

The at least one molecular receptor 22 is receptive to molecules having a predetermined and/or a preselected molecular structure. The at least one molecular receptor 22 can include either a biological molecule or a synthetic molecule having a specific affinity to its corresponding molecule. For example, each molecular receptor can include a chain of nucleotide bases to hybridize with a molecule having a complementary chain of nucleotide bases. In this case, each molecular receptor can include a DNA probe or a PNA probe for detecting a corresponding, complementary DNA base sequence, an RNA probe for detecting a corresponding, complementary RNA base sequence, or other DNA/RNA analogues.

The sensor 18 includes a first electrode 24 embedded in the gel 20. The first electrode 24 is used to electrically sense hybridization or binding of at least one molecule 26 to the at least one molecular receptor 22. For example, the at least one molecule 26 can include a molecule having a plurality of nucleotide bases such as a DNA fragment or an RNA fragment to hybridize with the at least one molecular receptor 22.

Preferably, the first electrode 24 includes an elongate portion embedded in the gel 20. More preferably, the elongate portion is linear.

Optionally, the sensor 18 further includes a second electrode 30 coupled to the gel 20. The second electrode 30 can be either directly coupled, capacitively coupled, or inductively coupled to the gel 20. The second electrode 30 assists in electrically sensing the hybridization or binding of the at least one molecule 26 to the at least one molecular receptor 22.

Preferably, the second electrode 30 is disposed at a side of the gel 20. Additionally, the second electrode 30 can surround at least a portion of the gel 20 and/or can surround at least a portion of the first electrode 24.

The second electrode 30 can include a cylindrical portion to surround or encircle the gel 20 and the first electrode 24. In this case, it is preferred that the first electrode 24 and the second electrode be generally coaxial. By "generally coaxial" it is meant that a first axis associated with the first electrode 24 is closer to being parallel to, rather than being perpendicular to, a second axis associated with the second electrode 30.

A meter 32 is electrically connected to the first electrode 24 and the second electrode 30. The meter 32 is used to electrically detect a binding event between the at least one molecule 26 and the at least one molecular receptor 22. Preferably, the meter 32 includes an impedance meter, such as a capacitance meter or an inductance meter, to measure and/or detect a change in impedance between the first electrode 24 and the second electrode 30 resulting from the binding event. Alternatively, the meter 32 can measure and/or detect a charge associated with the binding event, or can measure and/or detect a resonance shift resulting from the binding event.

Generally, the meter 32 can detect a change in an electrical quantity (measured between the first electrode 24 and the second electrode 30) between two instances of time (e.g. a pre-binding time and a post-binding time). Alternatively, the meter 32 can detect a change in an electrical quantity between the sensor 18 and a control sensor 34. The control sensor 34 can include a like gel having molecular receptors, a like first electrode, and a like second electrode as the sensor 18. The control sensor 34, however, is not exposed to the at least one molecule 26. The control sensor 34 is used as a calibration pixel for baseline subtraction.

Figure 2:
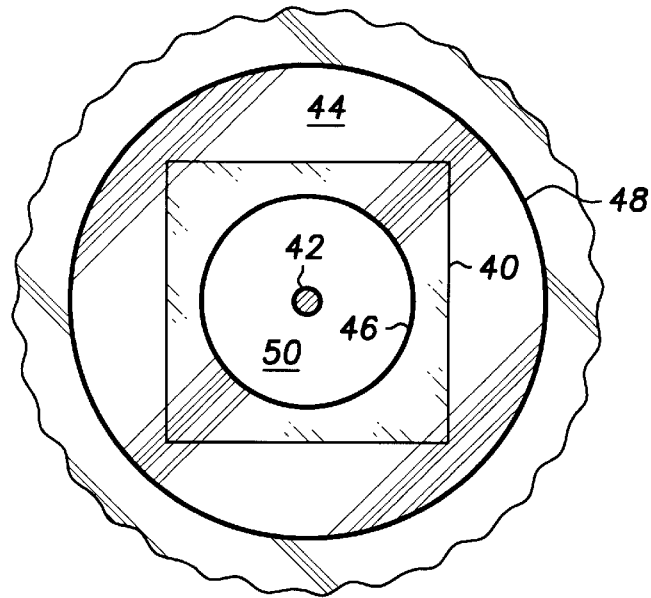
FIG. 2 is a top view of a first embodiment of a sensor in accordance with the present invention.

FIG. 2 is a top view of a first embodiment of a sensor in accordance with the present invention. The sensor includes a gel member 40. The gel member 40 supports a plurality of molecular receptors (not specifically illustrated) such as those described with reference to FIG. 1. Although illustrated to have a rectangular cross section, the gel member 40 can have an alternatively-shaped cross section. Examples of alternatively-shaped cross sections include, but are not limited to, a polygonal cross section, an elliptical cross section, and a circular cross section.

The sensor includes a first electrode 42 and a second electrode 44. The first electrode 42 is embedded within the gel member 40. The second electrode 44 is coupled to a surface of the gel member 40.

Preferably, the first electrode 42 is directly coupled to the gel member 40. In this case, the first electrode 42 can directly contact an inner surface of the gel member 40. Alternatively, the first electrode 42 can be capacitively coupled to the gel member 40. In this case, a dielectric material can be interposed between the first electrode 42 and a surface of the gel member 40.

Similarly, it is preferred that the second electrode 44 be directly coupled to the gel member 40. In this case, the second electrode 44 can directly contact a surface of the gel member 40. Alternatively, the second electrode 44 can be capacitively coupled to the gel member 40. In this case, a sheet of dielectric material can be interposed between the second electrode 44 and a surface of the gel member 40.

The second electrode 44 defines an inner periphery 46 and an outer periphery 48. The inner periphery 46 defines an opening 50 that is completely covered by the gel member 40. The surface of the gel member 40 coupled to the second electrode 44 is bounded within the outer periphery 48.

Preferably, the inner periphery 46 and the outer periphery 48 are circular-shaped so that the second electrode 44 has the shape of a circular ring. It is noted, however, that the inner periphery 46 and the outer periphery 48 can be alternatively shaped to provide an alternative annular shape for the second electrode 44.

Figure 3:
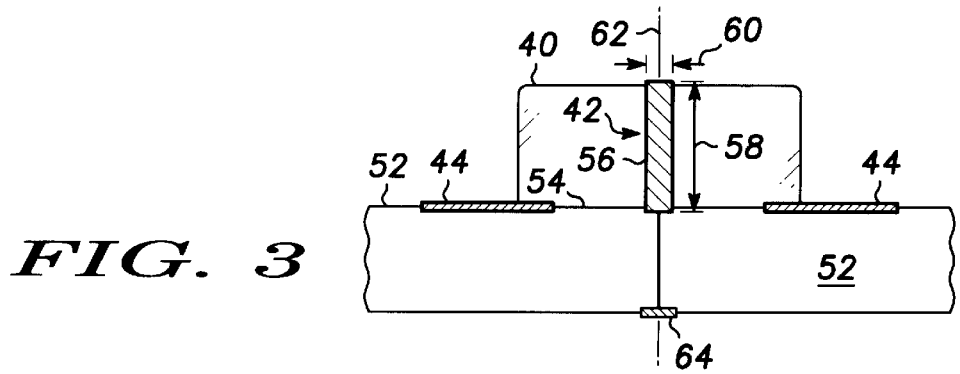
FIG. 3 is a side sectional view of the embodiment of the sensor of FIG. 2.

FIG. 3 is a side sectional view of the embodiment of the sensor of FIG. 2. As illustrated, the gel member 40, the first electrode 42, and the second electrode 44 are supported by a substrate 52. The substrate 52 has a surface 54 that supports the gel member 40. The second electrode. 44 is integrated with the substrate 52 at the surface 54.

The first electrode 42 includes an elongate portion 56 embedded in the gel member 40. The elongate portion 56 has a length 58 greater than its width 60. Although the elongate portion 56 can be nonlinear, it is preferred that the elongate portion 56 be linear. The elongate portion 56 is oriented along an axis 62 transverse to the surface 54 of the substrate 52 and a surface 64 of the second electrode 44. The axis 62 extends through the opening 50 of the second electrode 44.

It is preferred that the elongate portion 56 be generally normal to each of the aforementioned surfaces 54 and 64. By "generally normal" it is meant that an angle between the elongate portion 56 and a surface is greater than 45°. More preferably, the angle between the elongate portion 56 and each of the surfaces 54 and 64 is greater than 85°.

Preferably, the first electrode 42 extends through an entire dimension of the gel member 40 to provide an improved sensitivity for detecting binding events. Generally, the first electrode 42 can extend substantially through an entire dimension of the gel member 40, i.e. through at least 50% of a dimension of the gel member 40.

The first electrode 42 can be embedded in the gel member 40 using a variety of approaches. Using a first approach, the first electrode 42 includes a wire around which the gel member 40 is deposited. Using a second approach, the first electrode 42 includes a post fabricated by etching the substrate 52. The post is metallized before the gel member 40 is deposited.

Using a third approach, the substrate 52 is formed of a deformable material such as an elastic polymer or a plastic. A surface of the substrate 52 is metallized. An elongate member such as a pin is applied to an opposing surface of the substrate 52. The pin deforms the substrate 52 to form the first electrode 42. In this case, the first electrode 42 may have a cone-like shape. The gel member 40 can be deposited either prior to or subsequent to the deformation of the substrate 52.

The first electrode 42 can be electrically connected through the substrate 52 to a first contact 64. Optionally, the second electrode 44 can be electrically connected through the substrate 52 to a second contact.

Figure 4:
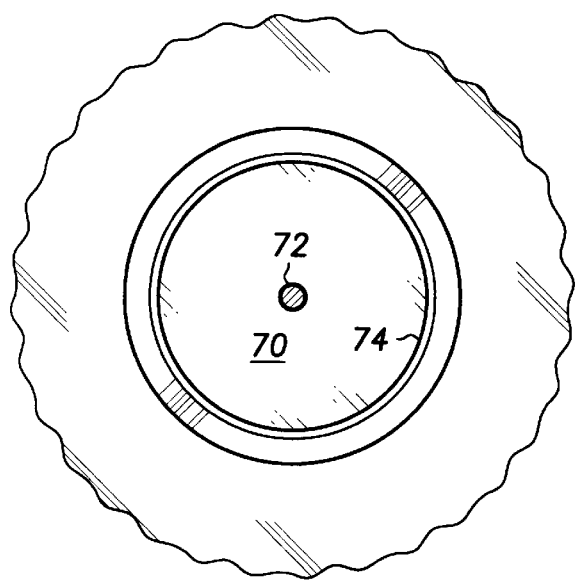
FIG. 4 is a top view of a second embodiment of a sensor in accordance with the present invention.

FIG. 4 is a top view of a second embodiment of a sensor in accordance with the present invention. The sensor includes a gel member 70. The gel member 70 supports a plurality of molecular receptors (not specifically illustrated) such as those described with reference to FIG. 1. Although illustrated to have a circular cross section, the gel member 70 can have an alternatively-shaped cross section. Examples of alternatively-shaped cross sections include, but are not limited to, a polygonal cross section such as a rectangular cross section, and an elliptical cross section.

The sensor includes a first electrode 72 and a second electrode 74. The first electrode 72 is embedded within the gel member 70. The second electrode 74 is coupled to a surface of the gel member 70.

Preferably, the first electrode 72 is directly coupled to the gel member 70. In this case, the first electrode 72 can directly contact an inner surface of the gel member 70. Alternatively, the first electrode 72 can be capacitively coupled to the gel member 70. In this case, a dielectric material can be interposed between the first electrode 72 and a surface of the gel member 70.

Similarly, it is preferred that the second electrode 74 be directly coupled to the gel member 70. In this case, the second electrode 74 can directly contact a side surface of the gel member 70. Alternatively, the second electrode 74 can be capacitively coupled to the gel member 70. In this case, a sheet of dielectric material can be interposed between the second electrode 74 and the side surface of the gel member 70.

The second electrode 74 is cylindrically shaped to surround the gel member 70 and the first electrode 72. Further, the second electrode 74 is coaxial with the first electrode 72.

Figure 5:
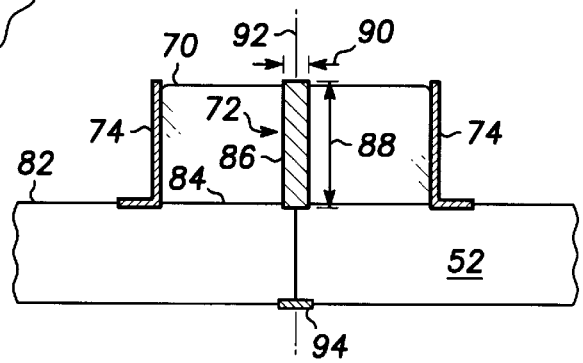
FIG. 5 is a side sectional view of the embodiment of the sensor of FIG. 4.

FIG. 5 is a side sectional view of the embodiment of the sensor of FIG. 4. As illustrated, the gel member 70, the first electrode 72, and the second electrode 74 are supported by a substrate 82. The substrate 82 has a surface 34 that supports the gel member 70.

The first electrode 72 includes an elongate portion 86 embedded in the gel member 70. The elongate portion 86 has a length 88 greater than its width 90. Although the elongate portion 86 can be nonlinear, it is preferred that the elongate portion 86 be linear. The elongate portion 86 is oriented along an axis 92 transverse to the surface 84 of the substrate 82. The axis 92 also serves as an axis along which the second electrode 74 is oriented.

It is preferred that the elongate portion 86 be generally normal to the surface 84. By "generally normal" it is meant that an angle between the elongate portion 86 and the surface 84 is greater than 45°. More preferably, the angle between the elongate portion 86 and the surface 84 is greater than 85°.

Preferably, the first electrode 72 and the second electrode 74 extend through an entire dimension of the gel member 70 to provide an improved sensitivity for detecting binding events. Generally, the first electrode 72 and the second electrode 74 can extend substantially through an entire dimension of the gel member 70, i.e. through at least 50% of a dimension of the gel member 70.

It is noted that the first electrode 72 can be formed and embedded in the gel member 70 using the approaches described with reference to FIG. 3.

The first electrode 72 can be electrically connected through the substrate 82 to a first contact 94. Optionally, the second electrode 74 can be electrically connected through the substrate 82 to a second contact.

Figure 6:
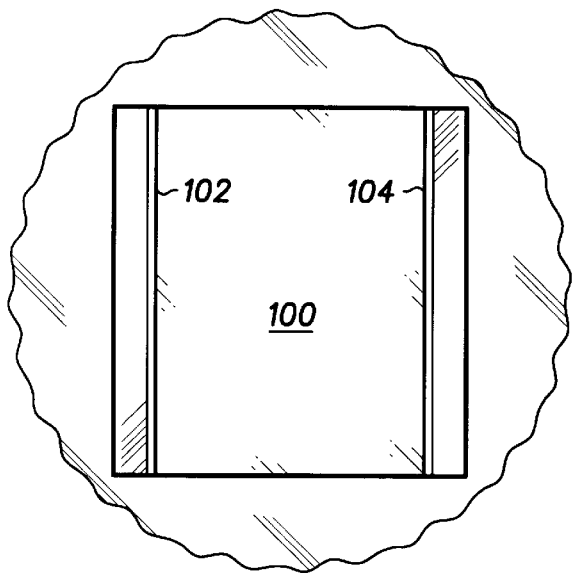
FIG. 6 is a top view of a third embodiment of a sensor in accordance with the present invention.

FIG. 6 is a top view of a third embodiment of a sensor in accordance with the present invention. The sensor includes a gel member 100. The gel member 100 supports a plurality of molecular receptors (not specifically illustrated) such as those described with reference to FIG. 1. Although illustrated to have a rectangular cross section, the gel member 100 can have an alternatively-shaped cross section. Examples of alternatively-shaped cross sections include, but are not limited to, a polygonal cross section, an elliptical cross section, and a circular cross section.

The sensor includes a first electrode 102 and a second electrode 104. The first electrode 102 is coupled to a first surface of the gel member 100. The second electrode 104 is coupled to a second surface of the gel member 100. Preferably, the first surface and the second surface are opposing surfaces of the gel member 100.

Preferably, the first electrode 102 and the second electrode 104 are directly coupled to the gel member 100. In this case, the first electrode 102 can directly contact the first surface and the second electrode 104 can contact the second surface. Alternatively, the first electrode 102 and the second electrode can be capacitively coupled to the gel member 100. In this case, a sheet of dielectric material can be interposed between the first electrode 102 and the first surface, and between the second electrode 104 and the second surface.

Figure 7:
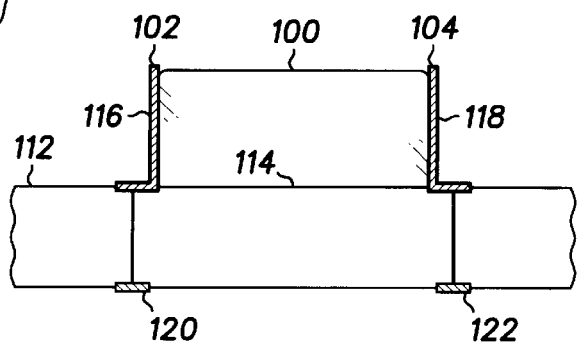
FIG. 7 is a side sectional view of the embodiment of the sensor of FIG. 6.

FIG. 7 is a side sectional view of the embodiment of the sensor of FIG. 6. As illustrated, the gel member 100, the first electrode 102, and the second electrode 104 are supported by a substrate 112. The substrate 112 has a surface 114 that supports the gel member 100.

The first electrode 102 includes a planar portion 116 that is generally normal to the surface 114. By "generally normal" it is meant that an angle between the planar portion 116 and the surface 114 is greater than 45°. More preferably, the angle between the planar portion 116 and the surface 114 is greater than 85°. Similarly, the second electrode 104 includes a planar portion 118 that is generally normal to the surface 114. Preferably, the planar portion 116 is generally parallel to the planar portion 118.

It is preferred that the first electrode 112 and the second electrode 114 extend along an entire side of the gel member 110 to provide an improved sensitivity for detecting binding events. Generally, the first electrode 112 and the second electrode 114 can extend substantially along an entire side of the gel member 100, i.e. along at least 50% of the side of the gel member 100.

The first electrode 102 can be electrically connected through the substrate 112 to a first contact 120. The second electrode 104 can be electrically connected through the substrate 112 to a second contact 122.

Figure 8:
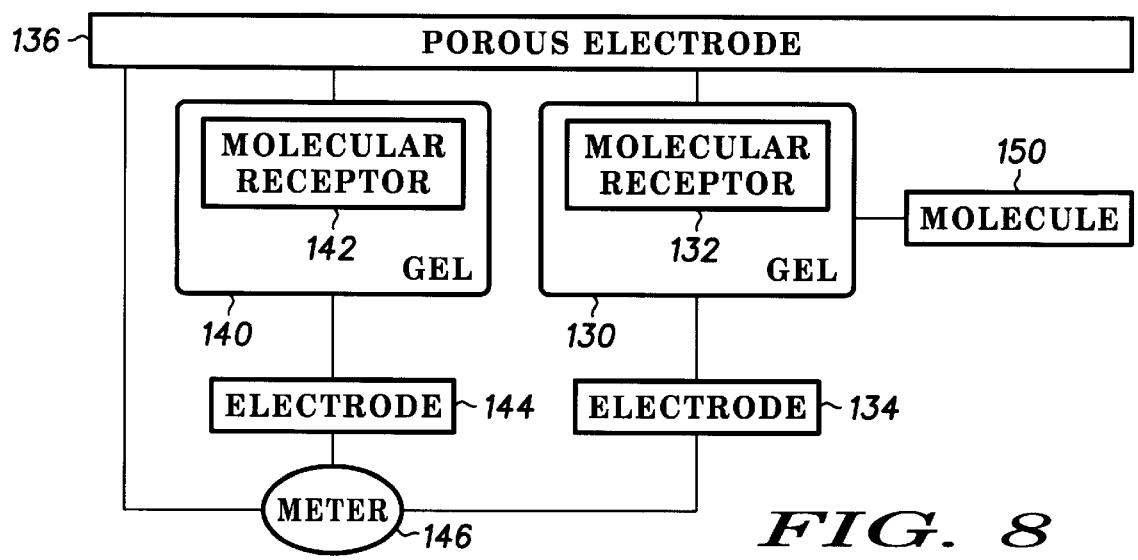
FIG. 8 is a block diagram of another sensor in accordance with the present invention.

FIG. 8 is a block diagram of another sensor in accordance with the present invention. The sensor comprises a first gel 130 which supports a first at least ore molecular receptor 132. The sensor further comprises a first electrode 134 and a porous electrode 136 coupled to the first gel 130. The first electrode 134 and the porous electrode 136 can be either directly coupled, capacitively coupled, or inductively coupled to the first gel 130.

The sensor can further comprise a second gel 140 which supports a second at least one molecular receptor 142. In this case, the second gel 140 has a second electrode 144 and the porous electrode 136 coupled thereto. The second electrode 144 and the porous electrode 136 can be either directly coupled, capacitively coupled, or inductively coupled to the second gel 140.

Molecules to be detected by the sensor migrate through the porous electrode 136 to at least one of the first gel 130 and the second gel 140. Examples of the porous electrode 136 include, but are not limited to, a wire mesh through which molecules can migrate, an electrode having a porosity which allows molecules to migrate there through, and a perforated electrode having one or more holes which allows molecules to migrate there through.

A meter 146, such as the meter 32, is electrically connected to the first electrode 134 and the porous electrode 136. The meter 146 is used to electrically detect a binding event between at least one molecule 150 and the first at least one molecular receptor 132. The at least one molecule 150 migrates through the porous electrode 136 to the first at least one molecular receptor 132. Similarly, the meter 146 can be electrically connected to the second electrode 144 to electrically detect a binding event for the second at least one molecular receptor 142.

Figure 9:
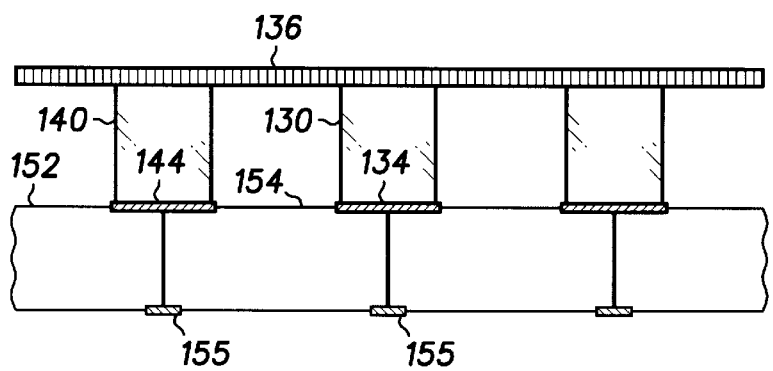
FIG. 9 is a side sectional view of an embodiment of the senscor of FIG. 8.

FIG. 9 is a side sectional view of an embodiment of the sensor of FIG. 8. The first electrode 134 and the second electrode 144 are supported by a substrate 152. The substrate 152 includes a surface 154 with which the first electrode 134 and the second electrode 144 are integrated. The first electrode 134 and the second electrode 144 are generally planar.

The first gel 130 is supported by the first electrode 134. Preferably, the first electrode 134 is directly coupled to the first gel 130. In this case, the first electrode 134 can directly contact a surface of the first gel 130. Alternatively, the first electrode 134 can be capacitively coupled to the first gel 130. In this case, a dielectric material can be interposed between the first electrode 134 and a surface of the first gel 130.

The second gel 140 is supported by the second electrode 144. Preferably, the second electrode 144 is directly coupled to the second gel 140. In this case, the second electrode 144 can directly contact a surface of the second gel 140. Alternatively, the second electrode 144 can be capacitively coupled to the second gel 140. In this case, a dielectric material can be interposed between the second electrode 144 and a surface of the second gel 140.

The porous electrode 136 is supported by the first gel 130 and the second gel 140. As a result, the first gel 130 is interposed between the porous electrode 136 and the first electrode 134, and the second gel 140 is interposed between the porous electrode 136 and the second electrode 144.

Preferably, the porous electrode 136 is directly coupled to the first gel 130 and the second gel 140. In this case, the porous electrode 136 can directly contact a surface of the first gel 130 and a surface of the second gel 140. Alternatively, the porous electrode 136 can be capacitively coupled to the first gel 130 and the second gel 140. In this case, a dielectric material can be interposed between the porous electrode 136 and each of the first gel 130 and the second gel 140.

The first electrode 134 and the second electrode 144 are electrically connected to contacts 155 through the substrate 152.

Each of the herein-described sensors can be included in an array of sensors. The array can include a one-dimensional array of sensors, a two-dimensional array of sensors, or a three-dimensional array of sensors. External contacts for interfacing the sensors to the meters 32 and 146 can be located at one or more edges of the array. Alternatively, the external contacts can be located at a surface opposite to a surface supporting the sensors and the gels.

A plurality of sensors described with reference to FIGS. 1 to 5, 13, and 14 can have their second electrodes interconnected to form a single ground electrode. Each sensor in the array is addressed by the single ground electrode and an external contact associated with its first electrode.

Figure 10:
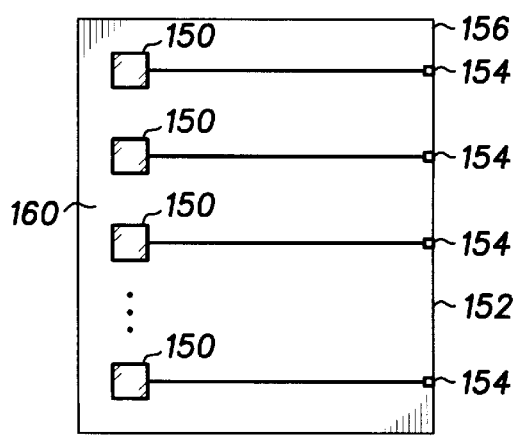
FIG. 10 illustrates an embodiment of a one-dimensional array of sensors.

FIG. 10 illustrates an embodiment of a one-dimensional array of sensors. A plurality of sensors 150 are integrated with a substrate 152. The sensors 150 are arranged as a linear array. A plurality of electrical contacts 154 are integrated with the substrate 152 near an edge 156. Each of the electrical contacts 154 is electrically connected to the first electrode of a respective one of the sensors 150.

A ground plane 160 can electrically interconnect the second electrodes of the sensors 150 for sensors described with reference to FIGS. 1 to 5. Alternatively, the ground plane 160 can comprise the porous electrode 136 described with reference to FIGS. 8 and 9.

Figure 11:
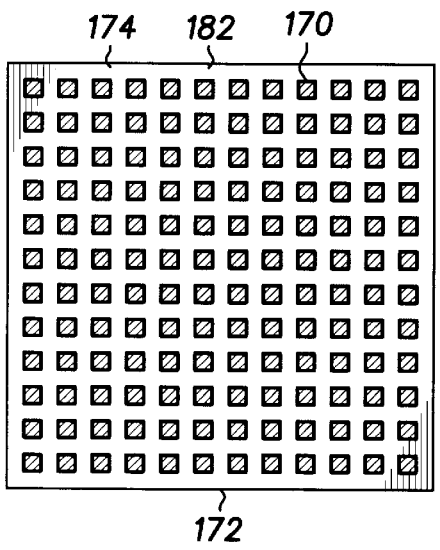
FIGS. 11 and 12 illustrate an embodiment of a two-dimensional array of sensors.
Figure 12:
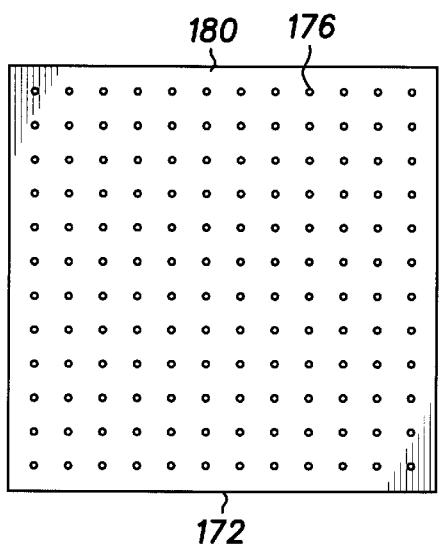

FIGS. 11 and 12 illustrate an embodiment of a two-dimensional array of sensors. A plurality of sensors 170 are integrated with a substrate 172 at a first surface 174. The sensors 170 are arranged as a two-dimensional array. A plurality of electrical contacts 176 are located at an opposite surface 180 of the substrate 172. Each of the electrical contacts 176 is electrically connected to the first electrode of a respective one of the sensors 170. Preferably, each of the electrical contacts 176 includes a pin oriented generally normal to the opposite surface 180 of the substrate 172.

A ground plane 182 can electrically interconnect the second electrodes of the sensors 170 for sensors described with reference to FIGS. 1 to 5. Alternatively, the ground plane 182 can comprise the porous electrode 136 described with reference to FIGS. 8 and 9.

Figure 13:
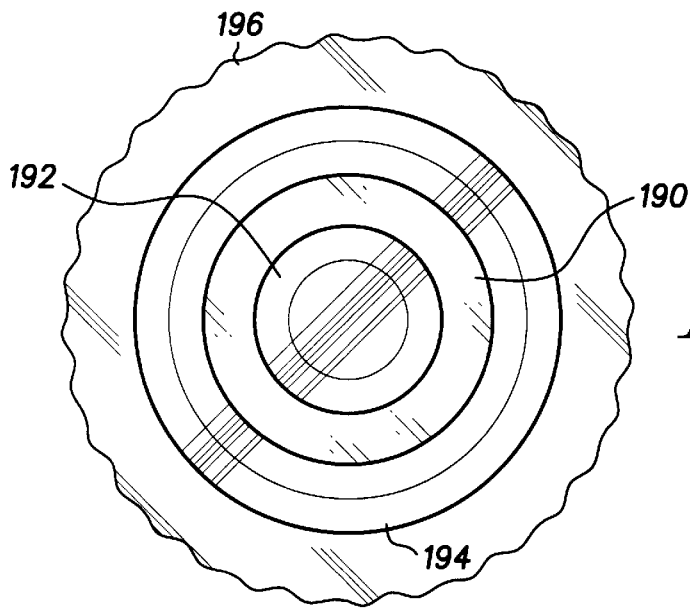
FIG. 13 is a top view of yet another embodiment of a sensor in accordance with the present invention.

FIG. 13 is a top view of yet another embodiment of a sensor in accordance with the present invention. The sensor includes a gel member 190. The gel member 190 supports a plurality of molecular receptors (not specifically illustrated) such as those described with reference to FIG. 1. The gel member 190 is annular shaped. The gel member 190 can have a circular, annular shape as illustrated, or can have an alternative annular shape.

The sensor includes a first electrode 192 and a second electrode 194. From the top view, the first electrode 192 is substantially surrounded by the gel member 190, and the second electrode 194 substantially surrounds the gel member 190.

Figure 14:
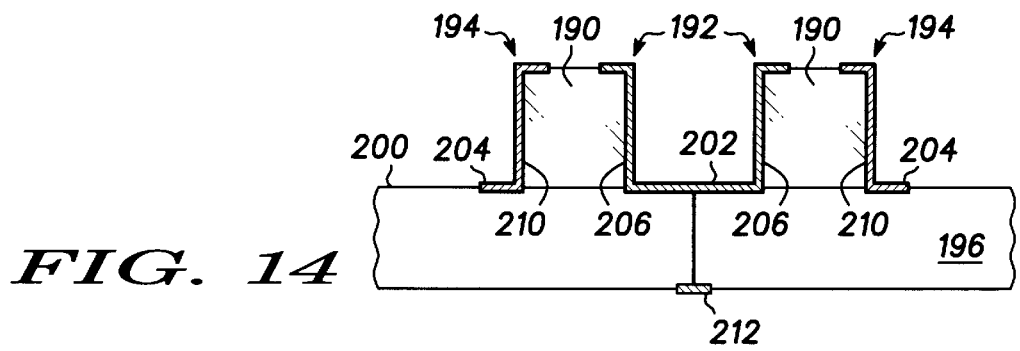
FIG. 14 is a side sectional view of the embodiment of the sensor of FIG. 13.

FIG. 14 is a side sectional view of the embodiment of the sensor of FIG. 13. As illustrated, the gel member 190, the first electrode 192, and the second electrode 194 are supported by a substrate 196. The substrate 196 has a surface 200 that supports the gel member 190, a portion 202 of the first electrode 192, and a portion 204 of the second electrode 194.

The first electrode 192 is coupled to an inner periphery 206 of the gel member 190. The second electrode 194 is coupled to an outer periphery 210 of the gel member 190. The first electrode 192 and the second electrode 194 can be either directly coupled or indirectly coupled to the gel member 190 as described earlier.

As illustrated, the sensor can include a bottom contact 212 electrically coupled to the first electrode 192. Alternatively, the sensor can include a top contact to the first electrode 192. Similarly, the second electrode 194 can have an external contact accessible at either the top, the bottom, or sides of the substrate 196.

For each of the herein-described embodiments of sensors for electrically sensing molecular binding events, it is preferred that the electrodes be formed of metal. In general, however, the electrodes can be formed of a conductive material or a semiconductive material. It is preferred that the herein-described substrates be formed of an elastic polymer or a plastic. In general, however, the substrates can be formed of a semiconductive material such as silicon or a dielectric material such as glass.

It is also noted that the gel members in each of the herein-described embodiments can be replaced by other receptor-supporting elements into which a reagent can diffuse. Examples of alternative elements include but are not limited to acrylomides, polypyrroles, polysaccharides, and other polymers.

Further, it is noted that embodiments of the present invention are applicable for biomolecular recognition in general. For example, the sensor can generally include ligand receptors for sensing hybridization, ligation, and analytes in solution.

Thus, there has been described herein several embodiments including preferred embodiments of sensors for electrically sensing molecular binding events for supported molecular receptors.

Because the various embodiments of the present invention electrically sense molecular binding events, they provide a significant improvement in that the use of radioactive markers and fluorescent markers is not required.

Additionally, various embodiments of the present invention as herein-described have an electrode embedded in each gel portion to provide better proximity to the molecular binding events.

Further, various embodiments of the present invention have a porous electrode coupled to each gel portion. The porous electrode is used to sense molecular binding events while allowing sample molecules to migrate there through.

It will be apparent to those skilled in the art that the disclosed invention may be modified in numerous ways and may assume many embodiments other than the preferred form specifically set out and described above. Accordingly, it is intended by the appended claims to cover all modifications of the invention which fall within the true spirit and scope of the invention.

What is claimed is:

1. A sensor comprising:
   a receptor-supporting element into which a reagent is diffusable;
   at least one molecular receptor supported within the receptor-supporting element; and
   a first electrode embedded in the receptor-supporting element.

2. The sensor of claim 1 wherein the at least one molecular receptor is receptive to a sequence of a plurality of nucleotide bases.

3. The sensor of claim 1 wherein the first electrode includes an elongate portion embedded in the receptor-supporting element.

4. The sensor of claim 3 further comprising a substrate having a surface to support the receptor-supporting element, wherein the first electrode is generally normal to the surface of the substrate.

5. The sensor of claim 3 wherein the elongate portion is linear.

6. The sensor of claim 1 further comprising a second electrode coupled to the receptor-supporting element.

7. The sensor of claim 6 wherein the first electrode and the second electrode are generally coaxial.

8. The sensor of claim 6 wherein the second electrode surrounds at least a portion of the first electrode.

9. The sensor of claim 6 wherein the second electrode is cylindrical.

10. The sensor of claim 6 wherein the second electrode is disposed at a side of the receptor-supporting element.

11. The sensor of claim 6 wherein the second electrode is annular-shaped.

12. The sensor of claim 6 wherein the second electrode contacts the receptor-supporting element.

13. The sensor of claim 6 wherein the second electrode surrounds a portion of the receptor-supporting element.

14. The sensor of claim 1 wherein the receptor-supporting element includes a gel.

15. A sensor comprising:
   a first receptor-supporting element;
   a first at least one molecular receptor supported within the first receptor-supporting element;
   a first electrode coupled to the first receptor-supporting element; and
   a porous electrode coupled to the first receptor-supporting element.

16. The sensor of claim 15 further comprising:
   a second receptor-supporting element;
   a second at least one molecular receptor supported within the second receptor-supporting element; and
   a second electrode coupled to the second receptor-supporting element;
   wherein the porous electrode is coupled to the second receptor-supporting element.

17. The sensor of claim 15 wherein the porous electrode comprises a porous mesh.

18. The sensor of claim 15 wherein the first receptor-supporting element is disposed between the first electrode and the porous electrode.

19. The sensor of claim 15 wherein the first electrode and the porous electrode contact the first receptor-supporting element.

20. The sensor of claim 15 wherein the first receptor-supporting element comprises a material selected from the group consisting of a gel, an acrylomide, a polypyrrole, and a polysaccharide.

21. A sensor comprising:
   a receptor-supporting element into which a reagent is diffusable;
   an annular-shaped electrode coupled to the receptor-supporting element; and
   an elongate electrode embedded in the receptor-supporting element.

22. A sensor comprising:
   an annular-shaped, receptor-supporting element into which a reagent is diffusable;
   at least one molecular receptor supported within the annular-shaped, receptor-supporting element; and
   a first electrode and a second electrode coupled to the annular-shaped, receptor-supporting element.

23. The sensor of claim 22 wherein the first electrode is coupled to an inner periphery of the annular-shaped, receptor-supporting element.

24. The sensor of claim 22 wherein the second electrode is coupled to an outer periphery of the annular-shaped, receptor-supporting element.

* * * * *